(12) United States Patent
Proksa et al.

(10) Patent No.: US 10,667,769 B2
(45) Date of Patent: Jun. 2, 2020

(54) METHOD OF COMPUTED TOMOGRAPHY IMAGING

(71) Applicant: KONINKLIJKE PHILIPS N.V., Eindhoven (NL)

(72) Inventors: Roland Proksa, Neu Wulmstorf (DE); Heiner Daerr, Hamburg (DE); Daniela Muenzel, Munich (DE); Peter Noel, Unterfohring (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 90 days.

(21) Appl. No.: 15/770,773

(22) PCT Filed: Nov. 1, 2016

(86) PCT No.: PCT/EP2016/076280
§ 371 (c)(1),
(2) Date: Apr. 25, 2018

(87) PCT Pub. No.: WO2017/080866
PCT Pub. Date: May 18, 2017

(65) Prior Publication Data
US 2018/0303436 A1 Oct. 25, 2018

(30) Foreign Application Priority Data
Nov. 10, 2015 (EP) ..................................... 15193957

(51) Int. Cl.
*G06K 9/00* (2006.01)
*A61B 6/03* (2006.01)
*A61B 6/00* (2006.01)

(52) U.S. Cl.
CPC ............ *A61B 6/032* (2013.01); *A61B 6/4241* (2013.01); *A61B 6/481* (2013.01); *A61B 6/482* (2013.01);
(Continued)

(58) Field of Classification Search
CPC ....... A61B 6/032; A61B 6/5205; A61B 6/504; A61B 6/481; A61B 6/4241; A61B 6/486; A61B 6/507; A61B 6/50; A61B 6/482
(Continued)

(56) References Cited

U.S. PATENT DOCUMENTS 5,833,613 A * 11/1998 Averkiou .................. A61B 8/06
  600/440
6,176,838 B1 * 1/2001 Sase ........................ A61B 6/481
  600/431
(Continued)

FOREIGN PATENT DOCUMENTS

JP 2009261519 A 11/2009
JP 2012090887 A 5/2012

OTHER PUBLICATIONS

Lv, et al., "Differentiation of Small Hepatic Hemangioma from Small Hepatocellular Carcinoma: Recently Introduced Spectral CT Method"; Radiology, vol. 259, No. 3, Feb. 25, 2011.

*Primary Examiner* — Van D Huynh
(74) *Attorney, Agent, or Firm* — Larry Liberchuk

(57) ABSTRACT

The invention relates to a method of Computed Tomography imaging comprising: a. Performing a single acquisition of image data from at least two contrast agents into a blood vessel network, a first contrast agent among said at least two contrast agents having been in said blood vessel network for a longer time than a second contrast agent among said at least two contrast agents, b. Processing said image data using K-Edge detection and/or iodine delineation to separate data associated with each contrast agents in order to obtain a concentration map of each contrast agent, c. Determining from said image data a first part of the blood vessel network comprising both the first contrast agent and the second contrast agent, and a second part of the blood vessel network comprising only the first contrast agent, d. Calculating a (Continued)

partial blood volume map of the first part of the blood vessel network based on the total amount of second contrast agent and on the concentration map of the second contrast agent, e. Calculating a partial blood volume map of the second part of the blood vessel network based on the total amount of first contrast agent, on the concentration map of the first contrast agent and on the partial blood volume map of the first part of the blood vessel network.

14 Claims, 3 Drawing Sheets

(52) U.S. Cl.
CPC ............... *A61B 6/50* (2013.01); *A61B 6/504* (2013.01); *A61B 6/507* (2013.01); *A61B 6/5205* (2013.01); *A61B 6/486* (2013.01)

(58) Field of Classification Search
USPC .......................................... 382/131
See application file for complete search history.

(56) References Cited

U.S. PATENT DOCUMENTS

| | | | |
|---|---|---|---|
| 8,208,699 B2* | 6/2012 | Hay | A61B 6/469 378/8 |
| 8,632,468 B2 | 1/2014 | Glossop | |
| 2002/0103437 A1* | 8/2002 | Jibiki | A61B 8/06 600/454 |
| 2004/0101088 A1* | 5/2004 | Sabol | A61B 6/481 378/4 |
| 2010/0094118 A1* | 4/2010 | Kobayashi | A61B 5/026 600/410 |
| 2010/0172562 A1* | 7/2010 | Satoh | G06T 7/0016 382/131 |
| 2011/0054295 A1* | 3/2011 | Masumoto | A61B 5/055 600/407 |
| 2011/0097273 A1* | 4/2011 | Proksa | A61B 6/501 424/9.1 |
| 2012/0070055 A1* | 3/2012 | Liu | G06T 7/0016 382/131 |
| 2012/0253190 A1* | 10/2012 | Gauthier | A61B 8/06 600/431 |

* cited by examiner

METHOD OF COMPUTED TOMOGRAPHY IMAGING

CROSS REFERENCE TO RELATED APPLICATIONS

This application is the U.S. National Phase application under 35 U.S.C. § 371 of International Application No. PCT/EP2016/076280, filed Nov. 1, 2016, published as WO 2017/080866 on May 18, 2017, which claims the benefit of European Patent Application Number 15193957.6 on Nov. 10, 2015. These applications are hereby incorporated by reference herein.

The invention relates a method and device to the field of medical imaging. It finds particular application to computed tomography (CT) angiography, especially for liver imaging.

BACKGROUND

Liver cancer is a major disease with about 750,000 death per year. Multi-phase Liver CT imaging is a major tool for diagnosis, staging and treatment monitoring. Multiple phases of the contrast agent dynamics are imaged and used to identify different lesion types. The liver has two blood supplies: the hepatic artery and the portal vein. As such, a contrast agent which has been injected at a given time will arrive at two different times in the aortic blood supply and in the portal blood supply of the liver. Since some lesion types behave differently in the contrast agent uptake and washout dynamics, it is of interest to image both the aortic and the portal subnetwork. For instance, whereas the liver parenchyma receives blood mainly from the portal venous system, tumors are usually fed by the hepatic artery.

The problem is that a dedicated CT protocol for evaluation of liver lesions contains up to four scans: a native scan, without any contrast agent, a second scan in the "arterial phase", when the contrast agent bolus just arrived in the arterial system, a third scan in the "portal venous phase" when the contrast agent bolus arrived through the portal vein, and a final scan when the system reached equilibrium.

Such an amount of scans exposes both the patient and the operators to a tremendous radiation dose which ought to be reduced. The invention addresses this issue while providing a way to calculate an exclusive blood map a first subnetwork of interest, for instance a portal blood map of the liver for evaluation of portal-venous blood supply of liver parenchyma, without contribution from another subnetwork contrast, for instance arterial contrast.

The method according to the invention is especially suited for multi-phase liver imaging but it can be used to image and map any set of blood subnetworks of interest.

It is known from U.S. Pat. No. 8,208,699 to perform multiple contrast agent injections, the delay between the injections being selected so that several regions of interest are predicted to be enhanced approximately at the same time.

Photon counting based spectral CT allows for quantitative and selective imaging of material with K-Edges within the X-Ray spectrum. It has been proposed in the past to use this imaging feature to perform Multi Phase Liver studies with multiple contrast agents. As an example if two contrast agents (CA1, CA2) have been administrated such that during one image acquisition CA1 is already in the portal phase while CA2 is still in the arterial phase. The differentiation of the two contrast agent phases can be performed by using the separation feature of K-Edge imaging. This technique can reduce the number of required scans and will therefore decrease the corresponding radiation dose significantly.

SUMMARY OF THE INVENTION

The present invention inter alia addresses additional techniques for multi contrast agents, multi-phase K-Edge CT imaging to enhance the diagnostic value of liver imaging.

The invention relates to a method of Computed Tomography imaging comprising:

a. Performing a single acquisition of image data from at least two contrast agents into a blood vessel network, a first contrast agent among said at least two contrast agents having been in said blood vessel network for a longer time than a second contrast agent among said at least two contrast agents, b. Processing said image data using K-Edge detection and/or iodine delineation to separate data associated with each contrast agents in order to obtain a concentration map of each contrast agent, c. Determining from said image data a first part of the blood vessel network comprising both the first contrast agent and the second contrast agent, and a second part of the blood vessel network comprising only the first contrast agent, d. Calculating a partial blood volume map of the first part of the blood vessel network based on the total amount of second contrast agent and on the concentration map of the second contrast agent, e. Calculating a partial blood volume map of the second part of the blood vessel network based on the total amount of first contrast agent, on the concentration map of the first contrast agent and on the partial blood volume map of the first part of the blood vessel network.

Said maps can find several applications, in particular these can be used for evaluation of portal-venous blood supply of liver parenchyma, without contribution from arterial contrast The blood vessel network can be an hepatic blood vessel network, comprising an arterial subnetwork, and a portal subnetwork, for instance in a way that said first part of the blood vessel network comprising the arterial subnetwork, and/or in a way that said second part of the blood vessel network comprising the portal subnetwork.

In a preferred embodiment of the invention, step b uses both K-edge detection and iodine delineation to separate the contrast agents. In that case, one contrast agent needs to include iodine. However, in alternate embodiments, step b can use only K-edge detection to separate the contrast agents. In that case, different K-edges are used.

Said at least two contrast agents can be of any type but, in a preferred embodiment, they are chosen such that they provide high sensitivity for photon counting based spectral CT and they can easily been delineated. Important parameter for the sensitivity is the contrast agent concentration, the effective Z, the attenuation step at the K-Edge and the K-edge energy relative to the X-ray spectrum of the scanner. For the delineation it is important to have sufficient separation of the K-edges. Other important factors are related to the chemistry of the contrast agents, the bio-compatibility, toxicity and other side effects to patients.

There can be any number of contrast agents. In particular, there can be as many contrast agents as there are regions of interest to be imaged: there is an interest to use three different contrast agents to image a system with three different blood supplies, four different contrast agents for a system with four different subnetwork etc. In case of liver imaging, and more generally in case there is an interest to image two different part of a blood vessel network simultaneously, the number of said at least two contrast agents is preferably exactly two. However there can be an interest to use a higher number of contrast agents even in that case. Specifically, in an alternate embodiment of the invention, three or more contrast agents are used, said contrast agents being chosen in order to cooperate between each other in order to better enhance the final images.

The method according to the invention can further include locating hypervascularized and/or hypovascularized zones. Such location can be of utter interest to help diagnose a hepatic tumor for instance.

The method according to the invention can be used as a preparation step before segmental resection of a liver.

As a matter of fact, CT imaging is an important imaging technique for a safe and efficient preparation of liver surgery. For segmental hepatectomy, knowledge of the segmental hepatic anatomy with its nutrient blood supply and also the venous and biliary drainage is essential for surgical planning Nowadays, information on the segmental anatomy is derived from the localization of vascular landmarks within the liver parenchyma. However, variants of portal venous anatomy are common, and it is important to know of the presence of such variants before performing hepatic surgery. Therefore, a dedicated visualization of the portal venous blood supply as shown in this invention will offer a significant improvement of preoperative planning for partial hepatectomy.

Another strategical approach in liver surgery includes preoperative embolisation of a segmental portal vein which supplies the liver segment which is planned to be resected. Segmental occlusion of the portal vein produces hepatic ischemia, resulting in atrophy of that segment and hypertrophy of the remaining healthy liver. This technique allows for a more extensive resection, which helps patients with extensive disease to undergo curative resection, and also reduces postoperative morbidity. Contrast mapping of portal venous enhancement using the method of the invention helps for a significant improvement in post interventional imaging following segmental portal venous embolisation, offering a direct visualization and quantification of the differences in portal venous blood supply of different liver segments.

The method according to the invention can also include storing the partial blood volume map of the first part of the blood vessel network and the partial blood volume map of the second part of the blood vessel network into a storage device. A database can then be generated out of the partial blood volume maps stored in said storage device. Such database could be used to help detect abnormalities on upcoming maps, hence increasing the diagnosis quality.

The invention also relates to a device configured to implement a method according to the invention. In particular, such device can include a medical X-ray scanner, for instance a medical CT scanner or another type of medical x-ray scanner such as a two dimensions X-ray scanner or a three dimensions X-ray scanner, equipped with photon counting detector technology providing sufficient energy resolution to enable K-edge imaging for at least one K-edge material. The device can further be equipped with means to inject two contrast materials consecutively into the patient. A reconstruction unit can be attached to generate two separate contrast agents maps/images based on K-edge or Iodine delineation. The device can further comprise means for calculating the desired arterial and portal blood maps and to visualize these results.

BRIEF DESCRIPTION OF THE FIGURES

The invention shall be better understood by reading the following detailed description of an embodiment of the invention and by examining the annexed drawing, on which.

DETAILED DESCRIPTION OF EMBODIMENTS

Figure 1:
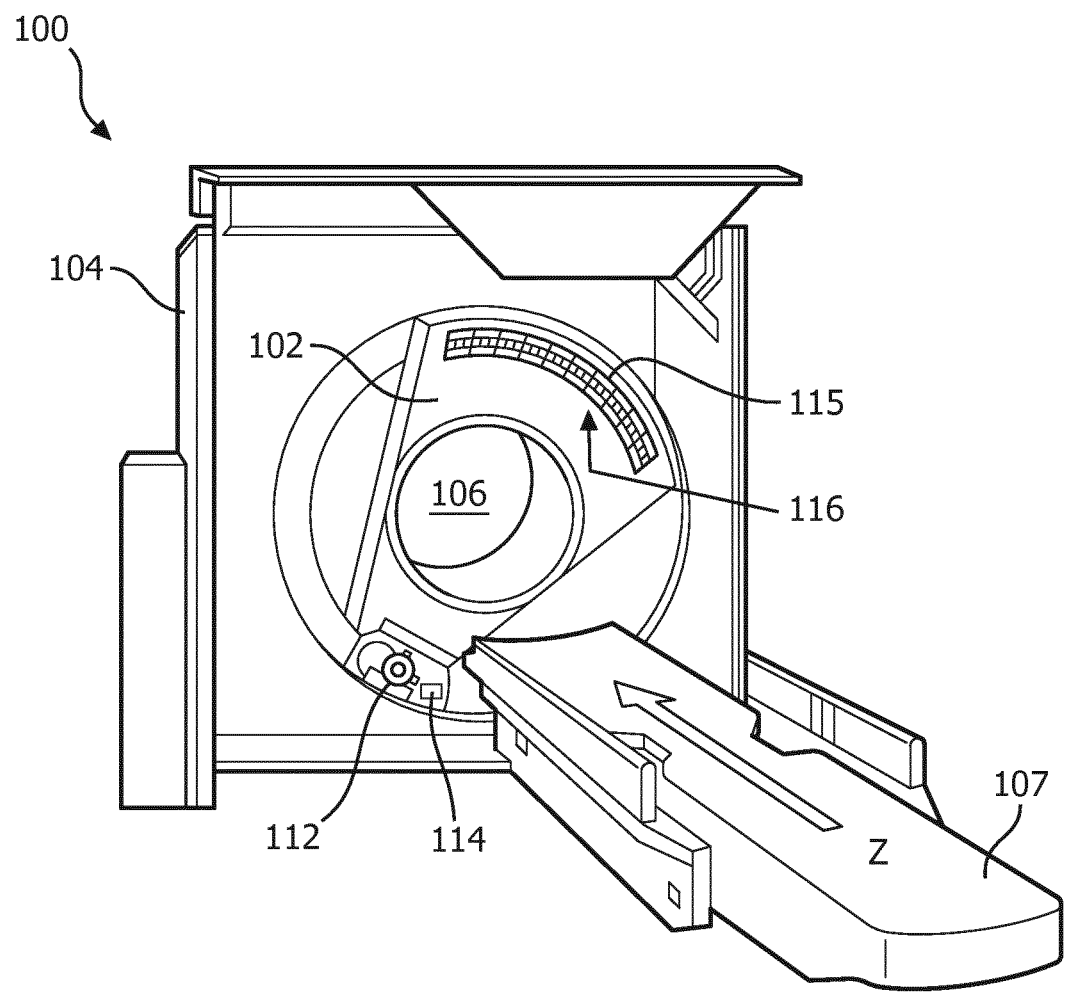
FIG. 1 is a typical Computed Tomography device.

FIG. 1 schematically illustrates an example imaging system 100, such as a computed tomography (CT) scanner. The imaging system 100 includes a rotating gantry 102 and a stationary gantry 104. The rotating gantry 102 is rotatably supported by the stationary gantry 104. The rotating gantry 102 is configured to rotate around an examination region 106 about a longitudinal or z-axis. The imaging system 100 further includes a subject support 107 that supports a subject or object in the examination region 106 before, during and/or after scanning. The subject support 107 can also be used to load and/or unload the subject or object into or from the examination region 106. The imaging system 100 further includes a radiation source 112, such as an x-ray tube, that is rotatably supported by the rotating gantry 102. The radiation source 112 rotates with the rotating gantry 102 around the examination region 106 and is configured to generate and emit radiation that traverses the examination region 106. The imaging system 100 further includes a radiation source controller 114. The radiation source controller 114 is configured to modulate a flux of the generated radiation. For example, the radiation controller 114 can selectively change a cathode heating current of the radiation source 112, apply a charge to inhibit electron flow of the radiation source 112, filter the emitted radiation, etc. to modulate the flux. In the illustrated example, the radiation source controller 114 modulates the flux based on a predetermined modulation pattern.

The imaging system 100 further includes a one or two dimensional array 115 of radiation sensitive detector pixels 116. The pixels 116 are located opposite the radiation source 112, across the examination region 106, detect radiation traversing the examination region 106, and generate an electrical signal (projection data) indicative thereof. In the illustrated example, the pixels 116 include direct conversion photon counting detector pixels. With such pixels, the generated signal includes an electrical current or voltage having a peak amplitude or a peak height that is indicative of the energy of a detected photon. The direct conversion photon counting detector pixels may include any suitable direct conversion material such as CdTe, CdZnTe, Si, Ge, GaAs or other direct conversion material.

Figure 2:
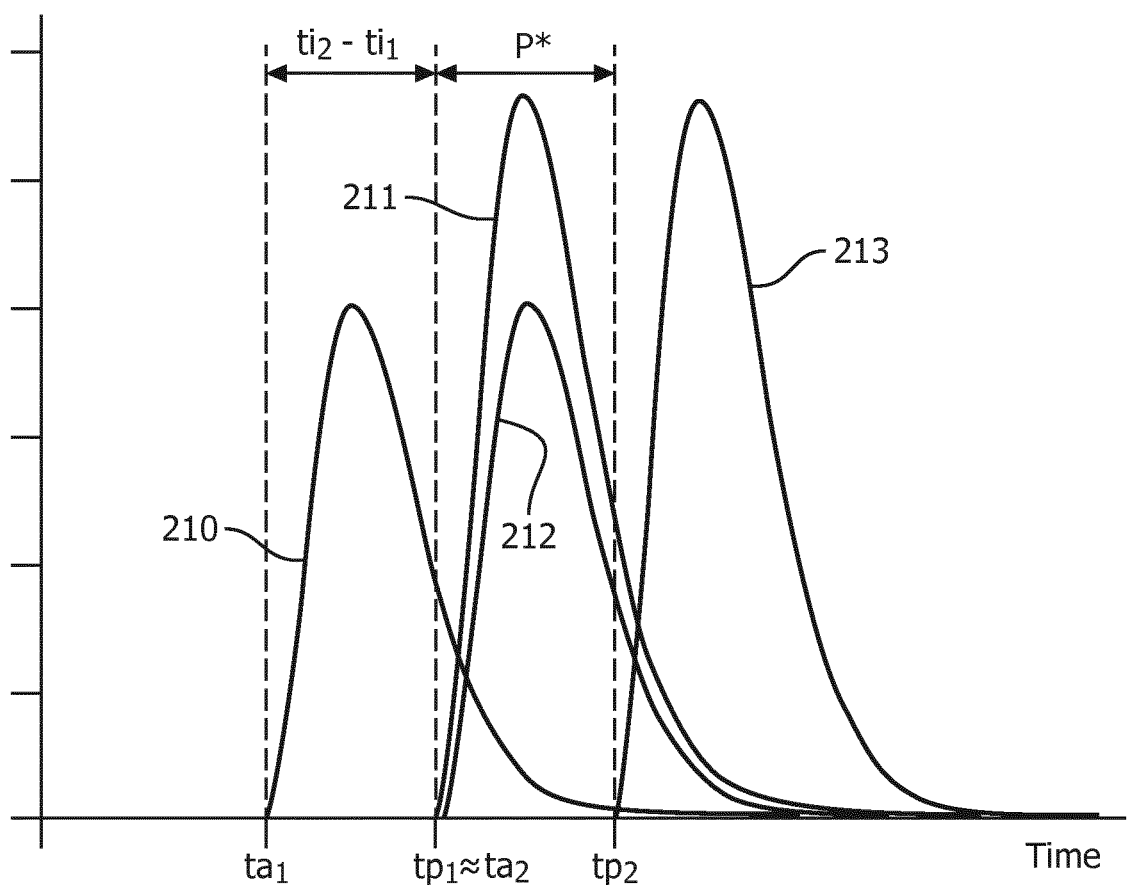
FIG. 2 represents the amount of contrast agent in each subnetwork over time.

For implementing a method according to the invention, the patient must have been previously injected with at least two contrast agents. In a preferred embodiment, the patient has been injected with a first contrast agent CA1 at a first time ti1, and then injected with a second contrast agent at a second time ti2. In a preferred embodiment, the method is used to image the liver and its portal and arterial blood supply network. FIG. 2 shows the amount of first contrast agent CA1 over time in the arterial (line 210) and portal (line 211) blood supply systems and the amount of second contrast agent CA2 over time in the arterial (line 212) and portal (line 213) blood supply network. The gap between ti2 and ti1, ti2-ti1, is chosen so as to approximately correspond to the time needed by contrast agent CA1 to reach the portal blood supply network (tp1), departing from the time it reaches arterial blood supply network (ta1). As such, assuming both contrast agents CA1 and CA2 navigate the general blood circulation at the same speed, contrast agent CA1 will start reaching the portal blood supply network (tp1) approximately at the same time contrast agent CA2 first reaches the arterial blood supply network (ta2). Therefore, there will be a period of time P* when there is a region of interest containing only the first contrast agent, namely the portal blood supply network, and another region of interest which contains both the first and the second contrast agent, namely the arterial blood supply network. Said period P* would start when contrast agent CA2 first reaches the arterial blood supply network (ta2≈tp1) and last until it reaches the portal blood supply network (tp2).

Figure 4:
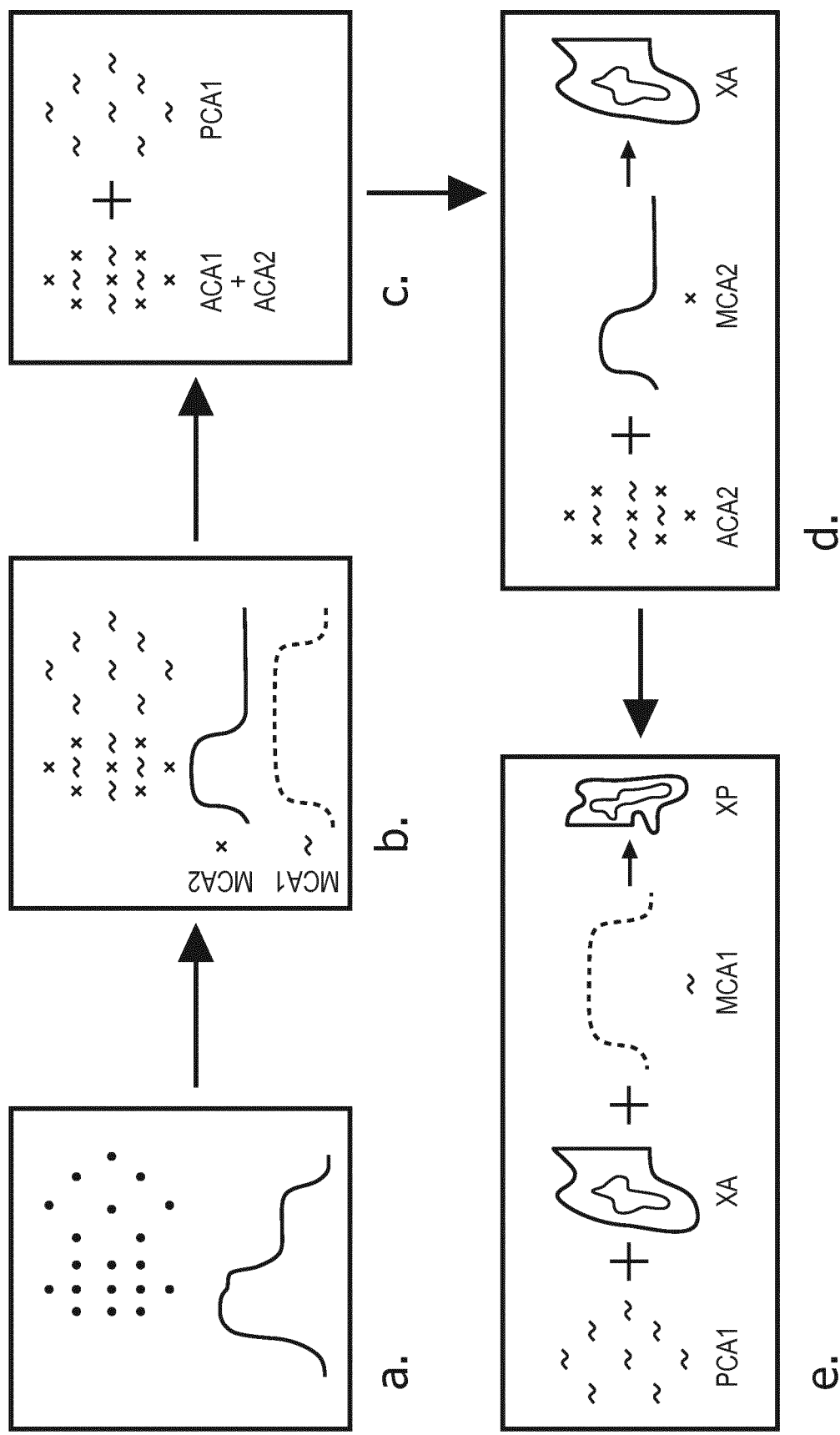
FIG. 4 is a flowchart corresponding to a method according to the invention.

In a preferred embodiment of a method according to the invention, simultaneous acquisition of image data from both the arterial and the portal blood supply network is performed, in a phase where CA1 is already in the portal phase while CA2 is still in the arterial phase, that is to say during period P*. This corresponds to step a of the diagram illustrated in FIG. 4. Since these images are acquired simultaneously, it is possible to use subtraction techniques to generate additional functional information without being effected by motion artefacts. With the use of K-Edge detection and/or iodine delineation, it is then possible to get a concentration map of both contrast agent CA1 and CA2 (MCA1 and MCA2), as illustrated schematically on step b of FIG. 4. It is then possible to identify a zone which contains only contrast agent CA1, which roughly corresponds to the portal blood supply network, and another zone containing both contrast agents CA1 and CA2, which roughly corresponds to the arterial blood supply network, as in step c of FIG. 4. Segmenting the arteries and the portal veins then allows measuring the related blood supply input function: ACA1 (arterial blood supply related to contrast agent CA1), ACA2 ((arterial blood supply related to contrast agent CA2), PCA1 (portal blood supply related to contrast agent CA1), and PCA2 (arterial blood supply related to contrast agent CA2, which should be equal to zero as there is no contrast agent CA2 in the portal blood supply network during P*).

In most case, it is reasonable to assume that the concentrations of the both CA are constant in the arteries as well as in the portal vein. By assuming further a negligible concentration gradient of the CA within the liver parenchyma and a fixed relation between CA uptake in the vessels and in the liver tissue the following model raises:

$$MCA2=XA*ACA2$$

$$MCA1=XA*ACA1+XP*PCA1$$

with XA and XP being the partial blood volume maps for arterial and portal blood. Step d of the method according to the invention, which is illustrated schematically in FIG. 4, consists in deriving XA from the first equation. It is then possible to estimate $XA*ACA1=ACA1*MCA2/ACA2$ and therefore derive XP, which corresponds to step e.

Figure 3:
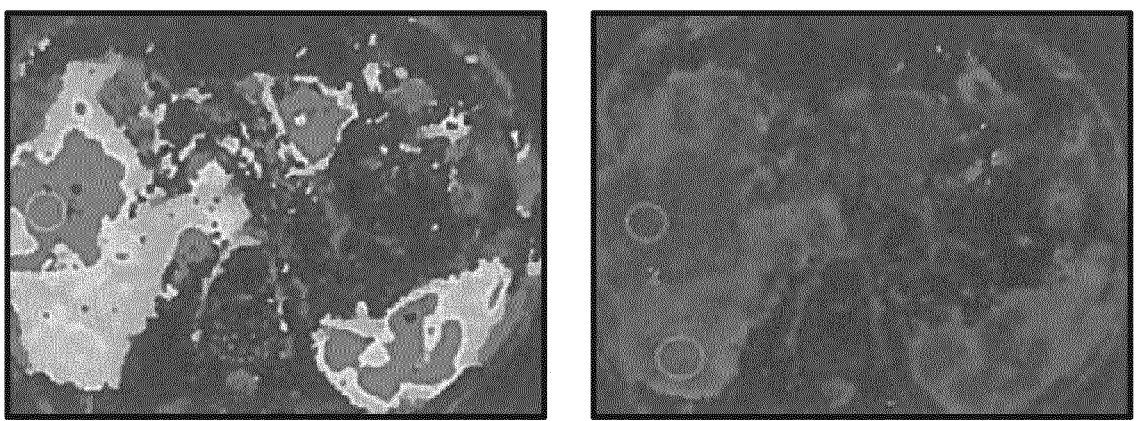
FIG. 3 represents a typical blood volume map of the arterial blood supply and of the portal blood supply of a liver, obtained from a method according to the invention.

Examples of actual partial blood volume maps of the arterial and portal blood supply network XA and XP are illustrated on FIG. 3.

A very interesting advantage of the method according to the invention resides in its clinical value as it allows deriving portal blood maps XP without contribution from atrial contrast.

The method according to the invention also allows to help a physician in establishing a diagnosis. As a matter of fact, differential diagnosis of hepatic lesions is mainly based on the observation of contrast enhancement. First, it is important to see if there is an uptake of contrast agent within the lesion, as, for example, cystic lesions of necrotic lesions do not enhance contrast agent. Therefore, it is necessary to compare images before (native) and after injection of contrast agent, both in the arterial blood supply network and in the portal blood supply network. In addition, liver lesions can be subdivided in hypervascularized lesions, which enhance intensely and early and hypovascularized tumors enhancing less and later. Different morphological patterns of contrast enhancement, for instance rim enhancement, peripheral nodular enhancement, "filling in", "wash-out", are the most important information for the radiologist to differentiate between benign lesions, like hemangiomas or focal nodular hyperplasia, and malignant tumors, e.g. metastases or hepatocellualar carcinoma. In MRI, image acquisition at different time points, with native scans and several other scans, up to 5 in routine diagnostic, is a standard procedure for evaluation of focal liver lesions. However, in CT, considerations on radiation dose are the main limitation, so the minimal version of a dedicated CT protocol for evaluation of a liver lesion will result in three scan acquisitions: a native scan and scans following the contrast agent administration in the arterial blood supply network and in the portal blood supply network.

The method according to the invention allows for the first time to extract native, arterial phase and portal-venous phase contrast enhanced images from a single CT scan acquisition. As a consequence, only one CT scan instead of three is necessary for diagnostic imaging of the liver in CT. As such, the informative value for characterization of liver lesions is significantly increased.

In addition, the method allows calculating an exclusive portal blood map of the liver as supplemental information about the portal-venous blood supply of the liver parenchyma. In standard CT, this information is masked by enhancement resulting from the arterial blood supply. This additional information offers a completely new feature for evaluation of the liver parenchyma, for example in patients with portal venous thrombosis, portal hypertension, or iatrogenic occlusion of a portal vein branch as a pre-therapeutic procedure before segmental resection of the liver.

While the invention has been illustrated and described in detail in the drawings and foregoing description, such illustration and description are to be considered illustrative or exemplary and not restrictive; the invention is not limited to the discussed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A method of Computed Tomography imaging, comprising:
   performing a single acquisition of image data from at least two contrast agents into a blood vessel network, a first contrast agent among said at least two contrast agents having been in said blood vessel network for a longer time than a second contrast agent among said at least two contrast agents;
   processing said image data using K-Edge detection and/or iodine delineation to separate data associated with each contrast agents in order to obtain a concentration map of each contrast agent;
   determining from said image data a first part of the blood vessel network comprising both the first contrast agent and the second contrast agent, and a second part of the blood vessel network comprising only the first contrast agent;
   calculating a partial blood volume map of the first part of the blood vessel network based on the second contrast agent and on the concentration map of the second contrast agent; and,
   calculating a partial blood volume map of the second part of the blood vessel network based on the first contrast agent, on the concentration map of the first contrast agent and on the partial blood volume map of the first part of the blood vessel network.

2. The method according to claim 1, said blood vessel network being an hepatic blood vessel network, comprising an arterial subnetwork, and a portal subnetwork.

3. The method according to claim 2, said first part of the blood vessel network comprising the arterial subnetwork.

4. The method according to claim 2, said second part of the blood vessel network comprising the portal subnetwork.

5. The method according to claim 1, further comprising using both K-edge detection and iodine delineation to separate the contrast agents.

6. The method according to claim 1, further comprising using only K-edge detection to separate the contrast agents.

7. The method according to claim 1, wherein the number of said at least two contrast agents is exactly two.

8. The method according to claim 1, further comprising locating hypervascularized zones.

9. The method according to claim 1, further comprising locating hypovascularized zones.

10. The method according to claim 1, further comprising a preparation before segmental resection of a liver.

11. The method according to claim 1, further comprising storing the partial blood volume map of the first part of the blood vessel network and the partial blood volume map of the second part of the blood vessel network into a storage device.

12. The method according to claim 11, further comprising generating a database out of the partial blood volume maps stored in said storage device.

13. A Computed Tomography device configured to implement a method according to claim 1, comprising:
    a medical x-ray scanner equipped with photon counting detector technology providing sufficient energy resolution to enable K-edge imaging for at least one K-edge material;
    means for injecting at least two contrast materials consecutively into the patient;
    a reconstruction unit configured to generate two separate contrast agents maps/images based on K-edge or Iodine delineation; and
    means for calculating and visualizing arterial and/or portal partial blood volume maps.

14. A non-transitory computer readable storage medium encoded with computer readable instructions, which, when executed by a processor, causes the processor to perform a method according to claim 1.

* * * * *